the# United States Patent [19]

Klein et al.

[11] Patent Number: 4,713,001
[45] Date of Patent: Dec. 15, 1987

[54] ORTHODONTIC BRACKET-MOUNTED TRACTION HOOK

[76] Inventors: Paul E. Klein, 928 Lake Shore Road; Douglas J. Klein, 901 Lake Shore Road, both of Lake Oswego, Oreg. 97034

[21] Appl. No.: 900,330
[22] Filed: Aug. 25, 1986
[51] Int. Cl.[4] ............................................. A61C 7/00
[52] U.S. Cl. .................................................... 433/18
[58] Field of Search ..................... 433/11, 10, 15, 18, 433/21

[56] References Cited

U.S. PATENT DOCUMENTS

| | | | |
|---|---|---|---|
| 1,589,782 | 6/1926 | Angle | 433/15 |
| 2,548,864 | 4/1951 | Brusse | 433/11 |
| 3,959,880 | 6/1976 | Andrews | 433/11 |
| 4,193,195 | 3/1980 | Merkel et al. | 433/13 |
| 4,522,590 | 6/1985 | Pletcher | 433/15 |

Primary Examiner—Robert Peshock
Attorney, Agent, or Firm—Kolisch, Hartwell & Dickinson

[57] ABSTRACT

An orthodontic traction-hook device which is adapted for selective, removable attachment to posts in an orthodontic bracket. The device includes spaced, interconnected legs that are releasably engageable with such posts, and a projection operatively joined to such legs for receiving an orthodontic, traction-applying instrumentality, such as a conventional orthodontic elastomer unit.

9 Claims, 10 Drawing Figures

ORTHODONTIC BRACKET-MOUNTED TRACTION HOOK

BACKGROUND AND SUMMARY OF THE INVENTION

This invention pertains to an orthodontic traction hook, and more particularly to such a hook which may be mounted conveniently and removably on posts in a conventional orthodontic bracket.

There are many applications in the practice of orthodontics, such as in so-called Class II and Class III traction conditions, where it is desirable and necessary to have hooks properly placed on other hardware present in a patient's mouth.

In the past, such hooks, which may only be required for limited periods of times, have been provided in a number of different ways that have not been entirely convenient. For example, specialized brackets are available which come permanently equipped with a projecting hook. Once such a bracket is mounted on a tooth, the hook remains, essentially, permanently in place, although its use may only be required for a limited time period during orthodontic treatment. Other kinds of hook devices are available which are prepared for tieing onto posts in a bracket and/or onto an in-place archwire. Mounting of these devices is expensive and time consuming, as is demounting when they are no longer required. Other techniques have included the soldering of hooks directly onto an archwire, as well as the bending or preforming of an archwire to have a hook-like protuberance. These approaches, as with the first one mentioned above, essentially result in a permanently present hook as long as the respective archwire is in place. Removal requires deligating of the particular archwire, removal, and replacement with a new one.

Another problem arises because of certain significant improvements in modern archwire materials. For instance, now widely available and often used titanium-based wires are literally impossible to attach to by soldering. Also, because of their extremely strong memory characteristics, they cannot successfully be bent sharply to form hooks.

A general object of the present invention is to provide a traction-hook device which obviates the handling difficulties, expenses and inconveniences which attend prior art devices and systems.

More particularly, an object of the invention is to provide a unique traction-hook device, configurable in a plurality of specific shapes, which is adapted for quick and easy removable attachment to posts in conventionally available orthodontic brackets.

According to a preferred embodiment of the invention, the same is adapted for removable attachment to at least a pair of the usual outwardly projecting posts in an orthodontic bracket, and more specifically, beneath the usual flanges in such posts which define inwardly facing, spaced channels. To this end, the device of the invention, in its preferred embodiment, includes: a pair of spaced, interconnected legs that are constructed for releasable securement in such posts' channels, with each leg disposed in a different channel; and a projection joined to these legs which is adapted to accommodate connection thereto, by hooking, of an orthodontic traction-applying instrumentality, such as a conventional orthodontic elastomer.

As will become apparent from the description below of various embodiments of the invention, a number of different shapes can be employed with desired, hook-like projections extending, selectively, in different predetermined directions relative to the respective brackets on which they are mounted.

The unique advantages offered by the invention will become immediately apparent. For example, a device made in accordance with the invention may easily and rapidly be installed on any desired bracket in a person's mouth, with or without an archwire being in place. Consequently, it offers an extremely convenient approach to the selective placement of hooks when and where desired, without placement and removal operations requiring time-consuming tieing in place, expensive soldering or welding, and/or removal of an archwire.

Various other objects and advantages which are attained by the invention will become more fully apparent as the description which now follows is read in conjunction with the accompanying drawings.

DETAILED DESCRIPTION OF THE INVENTION

Figure 1:
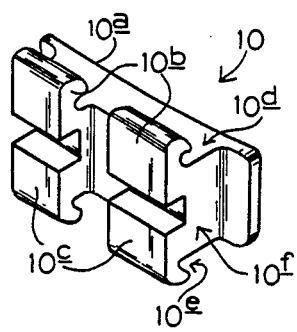
FIG. 1 is a perspective view of a conventional four-post orthodontic bracket in conjunction with which a preferred and other embodiments of the invention are disclosed herein.

As was mentioned above, FIG. 1 in the drawings provides a perspective view of a conventional four-post orthodontic bracket designated 10 in this figure. Bracket 10 includes the usual mounting base 10a, by way of which it is mounted on the usual tooth band or tooth surface, and four posts, including upper posts 10b and lower posts 10c.

As is well recognized by those skilled in the art, the oppositely and rearwardly extending flanges in the posts define inwardly facing, spaced channels, with the flanges in posts 10b defining a channel 10d, and those in posts 10c defining a channel 10e. On the front side of bracket 10, extending horizontally between and across the posts, is the usual archwire-receiving slot 10f.

Bracket 10, which is perhaps the most widely used orthodontic bracket today, has, accordingly, been chosen for the purpose of illustrating the preferred embodiment of the present invention, as well as certain modifications thereof. In order to simplify the drawings, bracket 10 is nowhere shown mounted on a tooth band, but rather is shown isolated, and as it appears relative to an installed traction-hook device made in accordance with the invention—all in relation to an installed archwire.

Figure 2:
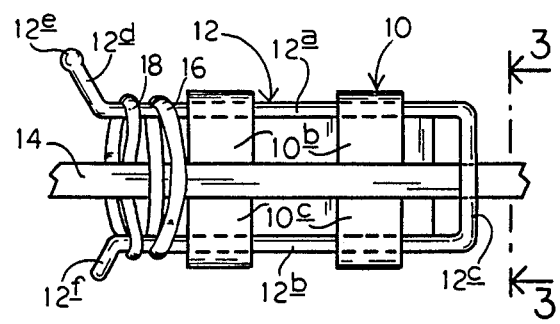
FIG. 2 is a fragmentary front view of the bracket of FIG. 1 showing a preferred embodiment of the invention mounted in place relative to this bracket, and relative to an archwire which is supported on the bracket.
Figure 3:
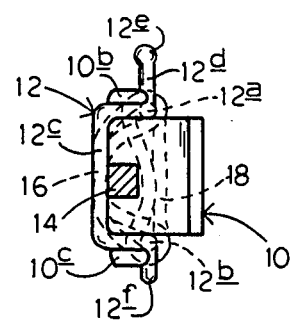
FIG. 3 is a view taken generally along the line 3—3 in FIG. 2.

Directing attention now to FIGS. 2 and 3, mounted on bracket 10 is a preferred embodiment 12 of a traction-hook device made in accordance with the invention. Device 12 which, in all embodiments disclosed herein, is formed from a single, elongate, wire-like element has a generally U-shaped body (as the same is viewed in FIG. 2) including a pair of spaced legs 12a, 12b joined through a stretch 12c. As can be seen particularly in FIG. 3, stretch 12c, which is also referred to as structure interconnecting the legs, is offset forwardly from what might be thought of as the plane containing legs 12a, 12b, and more specifically is offset toward the viewer in FIG. 2, and toward the left in FIG. 3. This offset is referred to as an archwire-clearance offset.

Continuing with the description of device 12, extending from the left end of leg 12a in FIG. 2 is an angularly upwardly extending hook, or projection, 12d, on the free end of which there is formed a bead 12e. Extending angularly downwardly from the left end of leg 12b in FIG. 2 is a short finger 12f.

As was mentioned earlier, device 12, in FIGS. 2 and 3, is shown mounted in operative position on bracket 10. Legs 12a, 12b are releasably received in the channels defined by the flanges in posts 10b, 10c, respectively, with stretch 12c extending over the front, outer side of an archwire 14 which is received in slot 10f. Securing device 12 in place are two, conventional, O-ring-shaped orthodontic elastomers 16, 18, each of which extends about the left ends of legs 12a, 12b, with elastomer 16 passing across the front side of the archwire and elastomer 18 passing across the rear side. In FIG. 2, the area where these elastomers are shown has been exaggerated in order to make their placement clear. This is also true with regard to later-discussed FIGS. 4, 6, 7 and 9.

The use and handling advantages offered by device 12 should be immediately apparent. It is easily installed on and removed from bracket 10 without having to remove or adjust archwire 14 in any way. Once in place, hook 12d is ready to be employed in a traction procedure simply by hooking the desired traction-applying structure, such as an orthodontic elastomer, onto it.

Another position in which device 12 can be used with stretch 12c extending across the front side of the archwire is with the device, in essence, rotated 180°, whereby hook 12d will extend downwardly and to the right at an angle relative to righthand post 10c in FIG. 2. A device which is an important companion to device 12 is a mirror-image of the latter. Such a device, in place, will have its stretch 12c extending over the front side of an archwire, with the option of having hook 12d extend upwardly and to the right relative to the bracket, or downwardly and to the left relative to the bracket.

Figure 4:
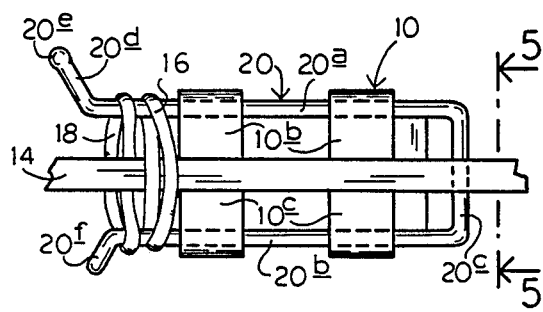
FIG. 4 is a view like FIG. 2 illustrating one alternative embodiment of the invention.
Figure 5:
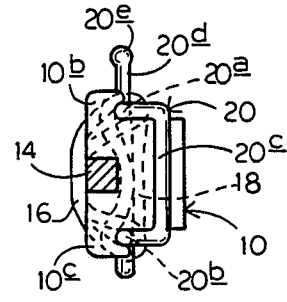
FIG. 5 is a view similar to FIG. 3 taken generally along the line 5—5 in FIG. 4.

FIGS. 4 and 5, which are like FIGS. 2 and 3, respectively, illustrate a traction-hook device 20 which, in all respects except one, is structurally identical to device 12. Because of this similarity, parts in device 20 which correspond to parts in device 12 have been given the same reference characters. The difference between device 20 and device 12 is that, in device 20, stretch 20c is offset rearwardly relative to the viewer in FIG. 4 (to the right in FIG. 5), so that it extends on the innerside of archwire 14. The relationship of device 20 to device 12 should be very obvious, as should too its capability of being rotated 180° to maintain stretch 20 on the inner side of the archwire to accommodate alternate positions and directions for hook 20d.

A companion, like that mentioned in connection with device 12 (a mirror image) is of course also possible in relation to device 20.

While it is possible to install and remove device 20 without removing archwire 14, it is more convenient to install this kind of device with the archwire removed. Because of this, a device like device 20 is ideally adapted for long-term, but nevertheless easily removable, placement in a person's mouth, whereas device 12 is probably best suited for shorter-term placements in a mouth.

Figure 6:
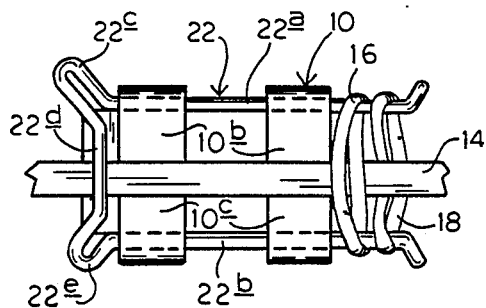
FIGS. 6 and 7 illustrate, respectively, two more embodiments of the present invention.

Turning attention now to FIG. 6, here at 22 there is shown another embodiment of a traction-hook device made in accordance with the present invention. The relationship between the structure of this device and those of the two devices just previously described ought to be readily apparent.

Device 22 includes a pair of legs 22a, 22b, the right ends of which have outwardly flared tips in FIG. 6, a hook, or projection, 22c which is formed by a reverse bend in the wire which makes up device 22, a forwardly offset stretch 22d which, like previously described stretch 12c, extends across the front side of archwire 14, and a downwardly projecting finger 22e which is formed in a reverse bend to join with the left end of leg 22b in FIG. 6. In this embodiment, one will note that hook 22c forms part of the structure which interconnects legs 22a, 22b.

Like the two other devices so far mentioned, device 22 may be rotated 180° to place hook 22c in a downwardly and rightwardly extending condition, still with stretch 22d extending across the front side of the archwire, also, it may have a mirror-image companion formed to allow stretch 22d to extend across the rear side of the archwire. Hook 22c is used in substantially the same manner as previously mentioned hooks 12d, 20d.

Figure 7:
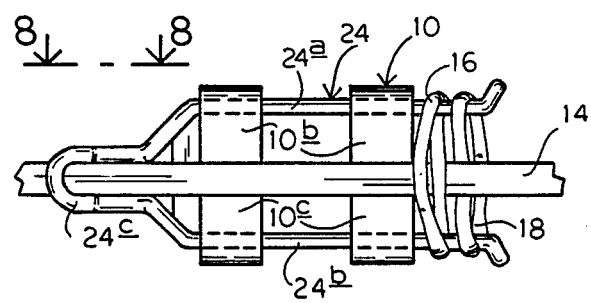
Figure 8:
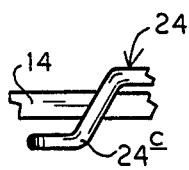
FIG. 8 is a fragmentary view taken generally along the line 8—8 in FIG. 7.

In FIGS. 7 and 8, another embodiment of a traction-hook device made in accordance with the invention is shown at 24. Device 24, which, like all of the other devices so far mentioned, is formed of a single, elongate, bent, steel wire, includes a pair of legs 24a, 24b which have outwardly flared tips on their right ends in FIG. 7. Extending between and joining the left ends of legs 24a, 24b in FIG. 7 is a compound-bend portion which forms a laterally, or generally horizontally, extending reverse-bend, forwardly offset hook, or projection, 24c. Hook 24c extends on the front side of archwire 14.

There are two principal ways in which hook 24c can be used in a traction application, vis-a-vis the way in which a traction-applying device is attached. In one way, the attaching end of the traction-applying device can encircle and thereby be caught by the entirety of hook 24c which defines an appropriate catch. In another application, an end of the traction-applying device can be slipped along the length of the element forming device 24 to become caught within the boundaries (catch) of the reverse bend portion that forms hook 24c. This, of course, would be done before device 24 is mounted on bracket 10.

Obviously, device 24c can be reversed 180° whereby, if the same were viewed as in FIG. 7, hook 24c would extend toward the right side of bracket 10.

Figure 9:
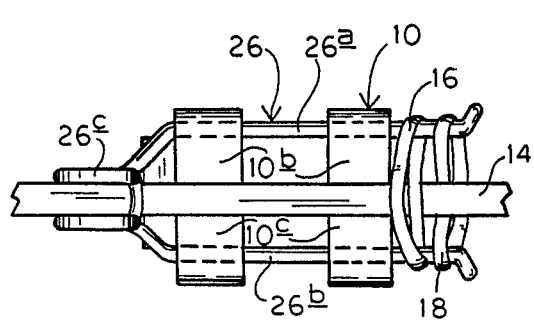
FIG. 9 is a view, like FIGS. 2, 4, 6 and 7, illustrating yet another embodiment of the invention.
Figure 10:
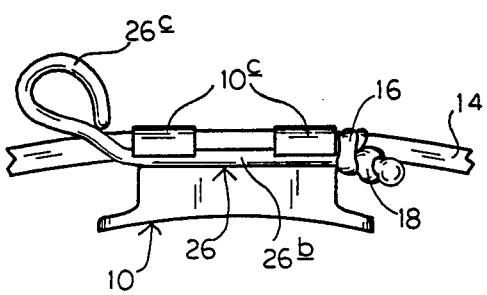
FIG. 10 is a view taken from the bottom side of FIG. 9.

FIGS. 9 and 10 illustrate one further embodiment, 26, of a traction-hook device made according to the invention. In all but one respect, device 26 is substantially the same as device 24. Thus device 26 includes a pair of spaced legs 26a, 26b joined, at their left ends in FIGS. 9 and 10, through a forwardly offset, compound-bend hook, or projection, 26c. As was true with previously described hook 24c, hook 26c extends toward the front side of archwire 14, but differs from hook 24c in that it includes another reverse bend which curls the tip of the hook backwardly toward bracket 10 to a point where it closes upon itself to form a catch.

Like device 24, device 26 can be rotated easily 180° to place the hook on the opposite side of bracket 10.

Thus, the important features and advantages of the invention should be clear. The structures of the various disclosed embodiments are extremely simple, and readily lend themselves to quick and easy mounting and demounting in operative positions at the selected locations on different brackets. In virtually every case, mounting and demounting can be accomplished whether or not an archwire is in place. These devices are readily suited for both long-term and short-term use, and, obviously, their installation and use does not involve any complicated soldering, welding, or tieing procedures.

Thus, while a preferred embodiment, and a number of important modifications, of the invention have been disclosed and described herein, other variations and modifications are certainly possible, and may be made without departing from the spirit of the invention.

It is claimed and desired to secure by Letters Patent:

1. An orthodontic traction-hook device adapted for selective, removable attachment to at least a pair of the outwardly projecting posts in an orthodontic bracket, where such posts include oppositely directed flanges which at least partially define inwardly facing, spaced channels, said device comprising
    a pair of spaced, interconnected legs constructed for releasable securement in such channels, with each leg disposed in a different channel, and
    a projection joined to said legs, adapted to accommodate the connection thereto, by hooking, of an orthodontic, traction-applying instrumentality, said projection, with the device mounted in place on a bracket, extending in spaced, freely exposed relation away from the latter.

2. An orthodontic traction-hook device adapted for selective, removable attachment to posts in an orthodontic bracket, said device comprising
    spaced, interconnected legs releasably engageable with such posts, and
    a projection operatively joined to said legs for receiving an orthodontic, traction-applying instrumentality, said projection, with the device mounted in place on a bracket, extending in spaced, freely exposed relation away from the latter.

3. An orthodontic traction-hook device adapted for selective, removable attachment to posts in an orthodontic bracket, said device comprising
    spaced, interconnected legs releasably engageable with such posts, and
    a projection joined to an end of one of said legs for receiving an orthodontic, traction-applying instrumentality, said projection, with the device mounted in place on a bracket, extending in spaced, freely exposed relation away from the latter.

4. An orthodontic traction-hook device adapted for selective, removable attachment to posts in an orthodontic bracket, said device comprising
    spaced, interconnected legs releasably engageable with such posts, and
    a projection taking the form of at least a portion of the structure interconnecting said legs, said projection being adapted for receiving an orthodontic, traction-applying instrumentality, said projection, with the device mounted in place on a bracket, extending in spaced, freely exposed relation away from the latter.

5. An orthodontic traction-hook device adapted for selective, removable attachment to posts in an orthodontic bracket, said device comprising
    spaced, interconnected legs releasably engageable with such posts, and
    a projection formed in the structure which interconnects said legs and including a reverse bend defining a catch for receiving an orthodontic, traction-applying instrumentality, said projection, with the device mounted in place on a bracket, extending in spaced, freely exposed relation away from the latter.

6. The device of claims 1, 2, 3, 4, or 5, wherein said legs form part of a continuous, bent, wire-like element.

7. The device of claims 1, 2, 3, 4, or 5, wherein the structure interconnecting said legs includes an archwire-clearance offset.

8. The device of claim 7, wherein said offset, in operative condition relative to an archwire, is disposed on the outer side of such archwire.

9. The device of claim 7, wherein said offset, in operative condition relative to an archwire, is disposed on the inner side of such archwire.

* * * * *